United States Patent [19]

Harding et al.

[11] Patent Number: 4,751,722
[45] Date of Patent: Jun. 14, 1988

[54] X-RAY APPARATUS

[75] Inventors: Geoffrey Harding, Hamburg; Josef M. Kosanetzky, Norderstedt; Ulrich Neitzel, Hamburg, all of Fed. Rep. of Germany; Peter Ypma, Eindhoven, Netherlands

[73] Assignee: U.S. Philips Corporation, New York, N.Y.

[21] Appl. No.: 56,295

[22] Filed: May 29, 1987

Related U.S. Application Data

[63] Continuation of Ser. No. 703,646, Feb. 21, 1985.

[30] Foreign Application Priority Data

Feb. 25, 1984 [DE] Fed. Rep. of Germany ....... 3406905

[51] Int. Cl.⁴ .......................................... G01N 23/201
[52] U.S. Cl. .......................................... 378/6; 378/88
[58] Field of Search .................................. 378/4, 6, 88

[56] References Cited

U.S. PATENT DOCUMENTS

| 3,936,638 | 2/1976 | Gibbons | 378/6 |
| 3,965,353 | 6/1976 | Macovski | 378/6 |
| 4,228,353 | 10/1980 | Johnson | 378/6 |
| 4,342,916 | 8/1982 | Jatteau et al. | 378/4 |
| 4,384,209 | 5/1983 | Wagner et al. | 378/14 |

FOREIGN PATENT DOCUMENTS 1476450 6/1977 United Kingdom .
2079563A 1/1982 United Kingdom .

OTHER PUBLICATIONS

Fenster, Aaron, "Split Xenon Detector for Tomochemistry in Computed Tomography", Journal of Computer Assisted Tomography, 1978, Jul., pp. 243-252.

Primary Examiner—Janice A. Howell
Attorney, Agent, or Firm—Jack E. Haken

[57] ABSTRACT

The invention relates to an X-ray apparatus which allows for the determination of the elastically scattered X-rays and the evaluation of the information contained therein. Because the scattered radiation exhibits a pronounced maximum value as a function of the scatter angle and because the scatter angle at which this maximum value occurs depends on the material in which the scattered radiation is produced, X-ray images thus formed contain essential information concerning the chemical composition of the body examined.

6 Claims, 2 Drawing Sheets

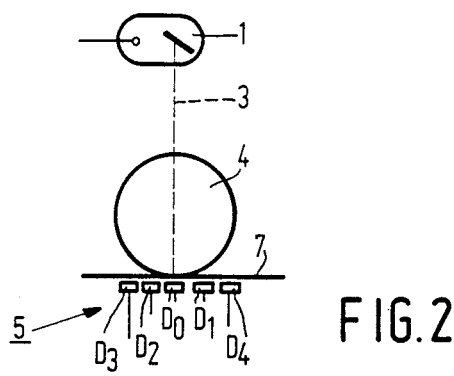
FIG. 2
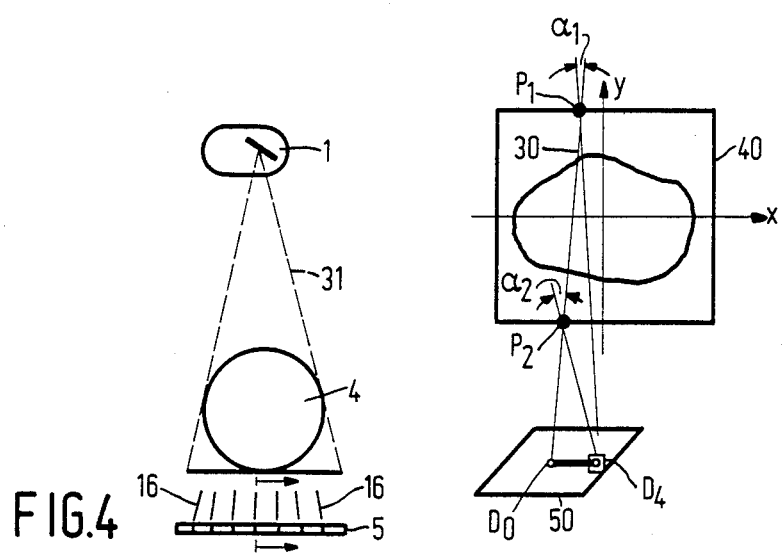
FIG. 4
FIG. 3
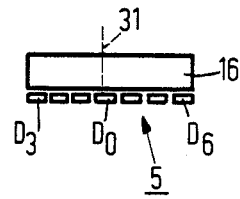
FIG. 5

X-RAY APPARATUS

This a continuation of application Ser. No. 703,646, filed Feb. 21, 1985.

The invention relates to an X-ray apparatus, comprising a radiation source which emits a primary beam having a small cross-section in at least one direction, and also comprising a detector array which is arranged at the other side of an examination zone and whose measurement values correspond to the one hand to the intensity of the primary radiation and on the other hand to that of the scattered radiation which emerges at a small angle with respect to the direction of the primary radiation.

An apparatus of this kind is known from British Pat. No. 1,476,450 in the form of a computer tomography apparatus which comprises a radiation source which emits a substantially flat, fan-shaped primary radiation beam which is intercepted by a plurality of first detectors at the other side of an examination zone. In addition to the primary radiation, however, these detectors also intercept scattered radiation which is caused by the primary radiation. In order to prevent an effect of this scattered radiation on the reconstruction, further detectors are arranged above and below the plane of the fan-shaped beam at a small distance from said first detectors, said further detectors intercepting only said scattered radiation and their output signals being subtracted from the output signals of the first detectors so that an image is obtained which is substantially free of scattered radiation.

From Med. Phys. 10(6), November/December 1983, pages 819 to 823, it is known that scattered radiation which encloses only a small angle with respect to the direction of the primary beam (for example, smaller than 12°) consists mainly of elastically scattered radiation. As opposed to non-elastically scattered radiation (Compton radiation), the energy spectrum of elastically scattered radiation corresponds to that of the primary radiation beam. Moreover, the elastic scattered radiation exhibits a very high angular dependency with a pronounced maximum which lies between 1° and 12°, depending on the irradiated material and the hardness of the scattered radiation.

Based on the recognition of the fact that the elastically scattered radiation also contains a substantial amount of information concerning the chemical condition of the irradiated material, it is the object of the invention to construct an X-ray apparatus of the kind set forth so that the elastic scattered radiation and its angular dependency can be used for the extraction of information.

This object is achieved in that the detector array supplies a plurality of scatter signals which characterize the intensities of the scattered radiation in different angular ranges, there being provided an arithmetic device which corrects the scatter signals in accordance with the attenuation of the primary beam, there also being provided a memory which stores the scatter signals processed by the arithmetic device for the various points of the examination zone, storage taking place in separate form according to scatter angle.

The detector array may comprise several detectors which are arranged at different angular distances from the primary radiation beam. However, use can alternatively be made of a detector (for example, an image intensifier) having a spatial resolution perpendicularly to the primary radiation beam. Becuase the elastic scattered radiation occurs in a comparatively small angular range with respect to the primary radiation beam, it passes approximately through the same body zone as the non-scattered primary radiation. Therefore, it may be assumed that it is attenuated by the body to the same extent as the primary radiation, so that it is comparatively simple to eliminate the effect of the attentuation of the scattered radiation by the body by a correction. The scatter signals thus processed and separately stored according to scatter angle can be used in various ways for the extraction of information.

For example, it is possible to produce a (two-dimensional) projection image of the measured integrals over the scatter angle. Furthermore, from a plurality of measured scatter integrals the scatter density distribution in a layer can be reconstructed. Both reproductions are possible for different scatter angles. However, it is also possible to mark one or more zones in an image which is a two-dimensional representation of the absorption distribution and to supply (mean) scatter densities therefor as a function of the scatter angle.

The invention can be used for all X-ray imaging methods in which the primary radiation beam has only a small dimension in the direction perpendicular to its propagation direction (pencil beam), even when several of such primary beams are used. However, the invention can also be used for X-ray imaging methods in which a fan-shaped primary beam (fan beam) is used, notably in third and fourth generation computer tomography apparatus. However, it is then necessary to take steps to ensure that the measurement results are not falsified due to the fact that a detector or a detector zone which is associated with a given beam path is exposed to elastic scattered radiation formed in another primary beam path.

The invention will be described in detail hereinafter with reference to the accompanying drawing. Therein:

FIG. 2 shows a second embodiment,

FIG. 3 shows a diagram illustrating the reconstruction method to be used in an embodiment as shown in FIG. 2, FIG. 4 shows a third embodiment, and FIG. 5 shows a detail of FIG. 4 which has been rotated through 90°.

Figure 1:
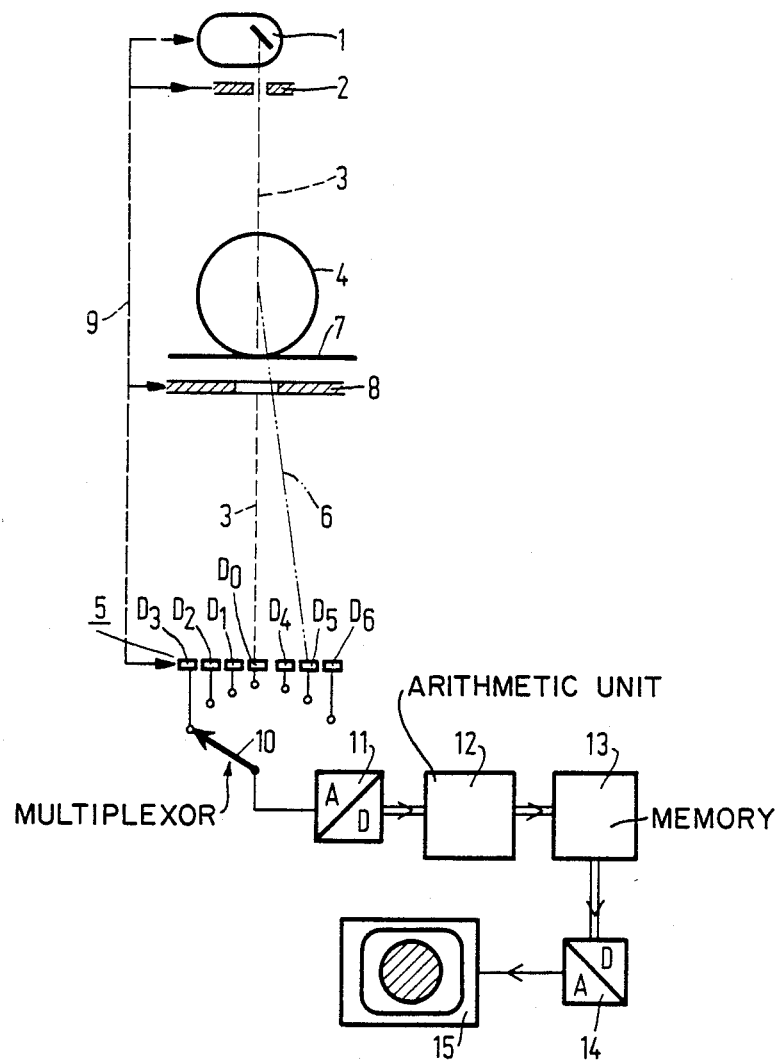
FIG. 1 shows a first embodiment.

The reference numeral 1 in FIG. 1 denotes a radiation source in the form of an X-ray source, a diaphragm 2 being arranged in the beam path thereof, said diaphragm forming a primary beam 3 which has a small cross-section perendicular to its propagation direction (pencil beam) and which passes through an examination zone with a body 4 which may be either a patient or a technical object. At the other side of the body 4, there is a detector array 5 which consists of a plurality of detectors $D_0 \ldots D_6$, one of which ($D_0$) is situated exactly in the primary beam 3, the other detectors $D_1$, $D_6$ being situated in a plane which is perpendicular to the primary beam or on a straight line in this plane and being arranged at different distances from the primary beam 3. The detectors $D_0 \ldots D_6$ are proportioned and arranged at such a distance from the body 4 that each detector can receive only the scattered radiation which emerges from the body 4 at a well-defined angle which is associated with the relevant detector. For the purpose of illustration, FIG. 1 merely shows a scattered ray 6 which is intercepted by the detector $D_5$. Between the body 4, the top 7 of an examination table, and the detector array 5 there is situated a further diaphragm 8 whose aperture is proportioned so that a straight connecting line between the primary beam 3 inside the body 4 and the outer detectors $D_3$ and $D_6$ can still pass through the aperture. However, it suppresses multiply scattered radiation. For example, when a point on the extreme right-hand side of the body 4 is struck by (Compton) scattered radiation and if this point itself emits scattered radiation again, at least the detectors $D_4$, $D_5$ and $D_6$ will be shielded against such scattered radiation. The multiply scattered radiation can be suppressed even better when between the detector array 5 and the body 4 laminations are arranged in such a manner that through these laminations each detector can cover only the part of the body which is traversed by the primary beam.

As is denoted by the broken line 9, the radiation source 1, the diaphragms 2 and 8 and the detector array 5 are mechanically coupled and displaceable perpendicular to the primary beam 3, so that other regions in the body 4 can be measured. It is also possible to displace this assembly in a second direction perpendicular to the primary beam 3, so that a two-dimensional projection image can be formed. However, the assembly can instead also be rotated through a small angle about an axis extending perpendicular to the plane of drawing, after which the assembly 1, 2, 5, 8 is displaced again as is customarily done in first generation computer tomography apparatus.

The measurement values supplied by the detectors are applied, via a multiplexer 10, to an analog-to-digital converter 11 having a linear or possibly logarithmic response curve in order to be processed in an arithmetic unit 12 which corrects the scatter signals in accordance with the attenuation of the primary radiation beam. For this purpose it is assumed that the scattered radiation which is produced by the primary beam 3 and which is emitted at a small angle essentially passes through the same body zone so that it is subject to substantially the same attenuation. For example, when an X-ray quantum is elastically scattered in the centre of a body and the maximum value of the energy is emitted at an angle of approximately 4° with respect to the primary beam, the points of emergence of the primary beam and the scattered beam at the periphery of the body will be situated only 1 cm apart, so that it is justified to assume the attenuation of the scattered beam and the primary beam to be equal. The attenuation of the primary beam, however, is known. It results from the ratio of the intensity of the primary radiation in front of and behind the body, the intensity before entry into the body being known whilst the intensity behind the body is measured by the detector $D_0$. For the correction of the scatter signals, therefore, they need be multiplied only by the attenuation factor of the primary beam 3 or an amount resulting from the attenuation factor must be added to the scatter signal obtained (when the measurement values obtained are converted into logarithmic form).

Subsequently, the scatter signals thus processed are applied to a digital memory 13 in which they are separately stored according to scatter angle. Therefore, the memory 13 must have a storage capacity which corresponds at least to the number of projections multiplied by the number of detector elements of the detector array 5.

The values stored can be extracted from the memory 13 again for the formation of an image.

When only the output signals of the detector $D_0$ are used, the reconstructed image will correspond to a conventional projection radiograph or a conventinal computer tomogram. However, when only the output signals of the detector $D_5$ (corrected in the arithmetic unit 12 by means of the signals of the detector $D_0$) are used for the formation of the image, a completely different image will be obtained and notably those materials will be represented which have the maximum value of the elastic scatter at an angle which corresponds to the angle enclosed by the beam 6 and the beam 3. However, when the signals of another detector are processed, another image will be obtained.

However, instead of a complete image, the information of only a part of the image could also be reproduced. For example, after the formation of an image derived from the output signals of the detector $D_0$, thus representing the absorption distribution in the regions of the body examined, a suitable region could be marked on the monitor by the user by means of a light pen and the like, the scatter density of said region being represented in a diagram (averaged across the marked region) as a function of the scatter angle.

When the body consists of an amorphous material, the scattered radiation will be circular-symmetrical with respect to the primary beam. This on the one hand enables the use of a detector which can intercept only a part of the scattered radiation which is emitted at a given angle; on the other hand it is thus possible to improve the sensitivity by using ring-shaped detectors which are concentric with the primary beam 3.

As a result of the spatial distribution of the detectors 5 in the embodiment shown in FIG. 1, i.e. their comparatively large distance from the body 4, it is achieved that each detector is struck only by scattered radiation which extends at a given angle with respect to the primary beam, said angle being permanently associated with the relevant detector. The values associated with the various positions of the X-ray source can thus be separately stored directly according to scatter angle. This relationship between a given detector and a solid angle, however, holds good only when the distance between the examination zone and the detector array is large in comparison with the dimensions of the examination zone. However, because of space requirements it is usually not possible to arrange the detector array at such a large distance from the examination zone.

Therefore, FIG. 2 shows an embodiment which is suitable for a computer tomography apparatus and in which the detector array 5 is arranged in the direct vicinity of the examination zone 4 or the body situated therein. With the exception of the detector $D_0$ which intercepts the primary beam 3 (and hence encloses the angle 0°), all other detectors receive scattered radiation at an angle which depends on the position in the examination zone in which the primary beam is elastically scattered. Each detector is thus associated with an angular range, the angular ranges of different detectors usually overlapping (it is to be noted that the maximum angle, taken with respect to, for example the centre of the examination zone, is smaller than shown in FIG. 2, said maximum angle amounting to, for example 12°). Because of the overlapping of the scatter angle ranges covered by the detectors, it is no longer possible to separate the scatter signals associated with different scatter angles from one another in such a manner that the output signals of the individual detectors of the detector array 5 are separately stored. The measured detector signals represent the integral value of the scatter in the object along the beam path. However, in such a computer tomography apparatus it is also possible to derive the scattered intensities separated according to scatter angle. This, however, is not directly measured as in the embodiment shown in FIG. 1; it is instead obtained by means of a reconstruction method. This method is based on a modified ART (ART—Algebraic Reconstruction Technique).

For an explanation of this method, reference is made to FIG. 3 in which the reference numeral 40 denotes the examination zone in which the absorption or scatter density distribution is to be determined. As is known, in computer tomography this examination zone is covered in successive steps by the primary beam 3 along a plurality of sets of parallel lines, each set of lines passing through the examination zone at a different angle. One of these straight lines is denoted by the reference numeral 30 in FIG. 3; it is characterized by its distance from the origin of the x—y coordinate system relating to the examination plane as well as by the angle enclosed by this straight line with respect to the x-axis or the y-axis of the system. Like any other primary beam, the primary beam extending along the straight line 30 is intercepted by the detector $D_0$ in the plane 50, whilst the scattered radiation is intercepted by the other detectors, only the detector $D_4$ thereof being shown for the sake of simplicity. The line 30 intersects the examination zone 40 at its upper edge in the point $P_1$ and in the point $P_2$ at its lower edge which faces the detector plane 50. The connecting line between the location of the detector $D_4$ and the point $P_1$ or $P_2$ intersects the line 30 at angles $\alpha 1$ and $\alpha 2$, respectively. This means that the detector $D_4$ intercepts the scattered radiation which is emitted at the angle $\alpha 1$ in the point $P_1$ and at the angle $\alpha 2$ in the point $P_2$, and that it intercepts the elastically scattered radiation which is scattered by points which are situated on the straight line 30 between the points $P_1$ and $P_2$ at an angle of between the angles $\alpha 1$ and $\alpha 2$.

In accordance with the invention, the scatter intensity for all pixels is set to an initial value, for example, equal to 0, in a memory in which the scatter intensity is stored as a function of x, y and $\alpha$. Subsequently, for each pixel situated on a straight line through the examination zone, for example the line 30, there is calculated the scatter angle $\alpha$ with which the radiation scattered in this pixel reaches the detector $D_4$. The intensity values associated in the memory with the position x, y of the pixel as well as the calculated scatter angle $\alpha$ are added. Image values for which no data are available for the given angle $\alpha$ are then determined by a interpolation from available data of neighbouring scatter angles. Subsequently, the difference is formed between the measurement values thus calculated and the measurement values corrected in accordance with FIG. 1 and this difference is distributed in a weighted manner as a correction among the combinations of x, y and $\alpha$ whose scatter density values have previously been added. Subsequently, the same procedure is repeated for the same line, but for the other detectors ($D_1 \ldots D_3$). After that the same procedure is repeated for another straight line which is parallel to the line 30 etc. until all lines which pass through the examination zone and which are parallel to the line 30 have been dealt with.

Subsequebtly, the described procedure is repeated for another set of lines which intersects the former set of lines at an adequately large angle, for example 45°. When all sets of lines associated with the various angular positions have thus been successively dealt with, the first iteration has been completed and a second iteration may commence; however, the second iteration is based on the scatter intensity values for the individual pixels x, y and the associated scatter angles which have been corrected by the first iteration. The number of iterations to be performed is determined on the basis of a termination criterion.

All correction facilities customarily used in the known ART methods as well as corrections for different angles of aperture of the individual detectors with respect to different pixels in the object can be used according to this method.

It follows from the foregoing that the electronic circuitry for the processing of the output signals of the detector array 5 can have the same construction in FIG. 2 as that in FIG. 1; however, the arithmetic unit 12 must then also perform the described ART procedure in addition to the attenuation correction of the scatter signals. The values ultimately produced by this method are transferred to the memory 13 and can be processed as described with reference to FIG. 1.

The apparatus shown in the FIGS. 1 and 2 enable the use of several primary beams instead of only one primary beam, said primary beams having a sufficiently large angular distance with respect to one another, for example like in second generation computer tomography apparatus. However, it is also possible to use the invention in apparatus operating according to the principle of third generation computer tomography apparatus. As is shown in FIG. 4, the radiation source 1 then emits a flat, fan-shaped primary beam 31 so that on the other side of the examination zone detectors are arranged on a straight line or on an arc of circle about the radiation source 1. With each of these detectors there is associated a number of further detectors which are situated, together with the detector which intercepts the primary radiation as well as the radiation source 1, in a plane which is perpendicular to the plane of the fan-shaped radiation beam (FIG. 5). However, a cross-talk problem is then encountered, i.e. scattered radiation produced in a beam path between the radiation source and one of the detectors intercepting the primary radiation could be intercepted by scattered radiation detectors which are not associated with the relevant detector. This would falsify the evaluation.

Such falsifications, however, can be eliminated by means of a number of flat laminations 16 which are situated between the examination zone 4 and the detector arrays 5 in planes which are perpendicular to the plane of the fan-shaped bean 31 and which intersect one another in the focus of the radiation source 1. When the dimension of these laminations is sufficiently large in the plane of drawing or the plane of the fan-shaped beam 31, these laminations are capable of substantially suppressing the scattered radiation which is produced along radiation paths whose intensity is not intercepted by the associated primary radiation detector. These laminations can at the same time also at least partly suppress the multiply scattered radiation mentioned with reference to FIG. 1; for further suppression, further laminations can be provided which are arranged to be substantially perpendicular to the former laminations and which are situated in planes which intersect one another in the centre of the object to be examined; the angle of aperture should then cover the entire beam path of the primary beam in the object.

What is claimed is:

1. X-ray apparatus comprising:

X-ray source means which direct a primary beam of X-rays, which beam has a small cross-section in at least one direction, along a plurality of paths through an adjacent examination zone;

detector means, disposed on a side of the examination zone opposite from the source means, which intercept and measure the intensity of radiation in the primary beam which has passed through the examination zone and which further intercept and measure the intensity of radiation which is elastically scattered from said primary beam within the examination zone and which emerges at an angle with respect to the primary beam;

means for storing the values of the intensity measured by the detector means for each of the paths through the examination zone;

means which correct the measured intensity values of the elastically scattered radiation as a function of the attenuation of radiation in the primary beam; and means which reconstruct an image of an object in the examination zone from the corrected values of the stored scattered radiation measurements.

2. Apparatus of claim 1 wherein the primary beam is a pencil beam which hs a small cross-section in two perpendicular directions.

3. Apparatus of claim 1 wherein the primary beam is a planar, fan-shaped beam which has a narrow cross-section in only one dimension.

4. Apparatus of claim 3 wherein the detector means comprise a first detector array which simultaneously measures radiation along a number of diverging paths within said fan-shaped beam and a plurality of additional detector arrays, disposed parallel to the first array, which measure the intensity of radiation which is elastically scattered at an angle with respect to the plane of the fan.

5. Apparatus as claimed in claim 1, 3 or 4 further comprising means disposed between the examination zone and the detector means which functions to partially suppress multiply scattered radiation.

6. Apparatus of claim 3 wherein the means which reconstructs an image functions to reconstruct a tomograph image in the plane of the primary beam using a modified algebraic reconstruction technique (ART).

* * * * *